United States Patent [19]
Fukuda et al.

[11] Patent Number: 5,981,498
[45] Date of Patent: Nov. 9, 1999

[54] AGENT FOR IMPROVING THE BLOOD CIRCULATION

[75] Inventors: Shigeharu Fukuda; Toshio Miyake, both of Okayama, Japan

[73] Assignee: Kabushiki Kaisha Hayashibara Seibutsu Kagaku Kenkyujo, Okayama, Japan

[21] Appl. No.: 09/188,405

[22] Filed: Nov. 10, 1998

[30] Foreign Application Priority Data

Dec. 9, 1997 [JP] Japan .................................. 9-354059

[51] Int. Cl.⁶ .................................................. A61K 31/70
[52] U.S. Cl. .............................................. 514/25; 514/23
[58] Field of Search ......................................... 514/25, 23

[56] References Cited

U.S. PATENT DOCUMENTS

| | | | |
|---|---|---|---|
| 5,145,781 | 9/1992 | Suzuki et al. | 435/99 |
| 5,494,667 | 2/1996 | Uchida et al. | 424/195.1 |
| 5,627,157 | 5/1997 | Hijiya et al. | 514/25 |

FOREIGN PATENT DOCUMENTS

| | | |
|---|---|---|
| 0387042 | 9/1990 | European Pat. Off. . |
| 0402049 | 12/1990 | European Pat. Off. . |
| 0420376 | 4/1991 | European Pat. Off. . |
| 0480640 | 4/1992 | European Pat. Off. . |
| 0486315 | 5/1992 | European Pat. Off. . |
| 0628630 | 12/1994 | European Pat. Off. . |
| 0688866 | 4/1995 | European Pat. Off. . |
| 0671470 | 9/1995 | European Pat. Off. . |
| 0674005 | 9/1995 | European Pat. Off. . |
| 0688867 | 12/1995 | European Pat. Off. . |
| 0691344 | 1/1996 | European Pat. Off. . |
| 0693558 | 1/1996 | European Pat. Off. . |
| 0697461 | 2/1996 | European Pat. Off. . |
| 0704531 | 4/1996 | European Pat. Off. . |
| 0709461 | 5/1996 | European Pat. Off. . |
| 7143876 | 6/1990 | Japan . |
| 37593 | 1/1991 | Japan . |
| 327293 | 2/1991 | Japan . |
| 358790 | 3/1991 | Japan . |
| 3115292 | 5/1991 | Japan . |
| 4179490 | 1/1992 | Japan . |
| 4144694 | 5/1992 | Japan . |
| 7213283 | 8/1995 | Japan . |
| 7298880 | 11/1995 | Japan . |
| 7322883 | 12/1995 | Japan . |
| 866187 | 3/1996 | Japan . |
| 866188 | 3/1996 | Japan . |
| 884586 | 4/1996 | Japan . |
| 8149980 | 6/1996 | Japan . |
| 8336388 | 12/1996 | Japan . |
| 99986 | 1/1997 | Japan . |

OTHER PUBLICATIONS

"Rinsho–Kensa–Koza" (Clinical Testing Course), vol. 11, pp. 115–135 (1985), published by Ishiyaku Shuppan Publishers, Inc., Tokyo, Japan.

Bulletin of the University of Tsukuba, School for the Blind, vol. 16, pp. 75–83 (1983).

*Primary Examiner*—Raymond Henley, III
*Attorney, Agent, or Firm*—Browdy and Neimark

[57] ABSTRACT

An agent for improving the blood circulation, which contains as an effective ingredient glycosyl vitamin P such as glycosyl hesperidin and glycosyl rutin. The agent improves the blood circulation in humans to effectively relieve muscular rigidity.

20 Claims, 2 Drawing Sheets

AGENT FOR IMPROVING THE BLOOD CIRCULATION

BACKGROUND OF THE INVENTION

1. Field of the Invention

The present invention relates to an agent for improving the blood circulation, and more particularly to an agent for improving the blood circulation containing glycosyl vitamin P as an effective ingredient.

2. Description of the Prior Art

As means for communicating information and for drafting documents have become diversified, variety types of Office Automated (OA) instruments are widely spread in work places including offices, as well as homes in general. OA instruments generally require users a posture of detaching the users' upper arms from their bodies during operation to cause STIFF in particular parts of the limbs, arms, backs, waists, etc., as a result of muscular rigidity caused by the users' relatively-long-time operation of the instruments. Generally, STIFF in the muscular may be easily relieved by grasping or massaging the stiff parts. However, in the case of operating OA instruments daily, if STIFF is once occurred, it could not be easily diminished. In addition to the operation of OA instruments, STIFF can be induced by factors such as physical exercise, physical labor, inappropriate posture, and mental stress or may be induced by diseases such as cervical spondylosis, thoracic outlet syndrome, hypertension, asthenopia, autonomic dystonia, and climacteric disturbance. Depending on the symptom of STIFF, particular slow pains and unpleasant feelings will last for a relatively-long period of time, and in some cases STIFF may accompany head ache and/or vomiting.

Although the mechanism of occurrence of STIFF is still not clear, it is deemed that excessive stimulation of nerves, muscular fatigues, and autonomic dystonia will trigger successive contraction of peripheral veins, disorder of the blood circulation in muscular, and congestion, causing a specific STIFF. Therefore, improvement of the blood circulation is effective to diminish muscular STIFF. Treatments such as massage, warm bath therapy, fomentation, electric stimulation, and administration are difficult to attain the desired effect, or some of them would be troublesome because patients should have to go hospitals for receiving professional treatments.

SUMMARY OF THE INVENTION

In view of the foregoing, the object of the present invention is to provide a daily-usable means for effectively improving the blood circulation with lesser side effects.

The present inventors studied biologically active substances to solve the above object. As a result, they found that glycosyl vitamin P as a vitamin improves the blood circulation, resulting in an effective exertion of a strong effect on relieving muscular rigidity induced by muscular stiffness in the shoulder and lumbago. They also found that the action of glycosyl vitamin P is significantly accelerated by trehalose, a disaccharide. Thus the present invention solves the above object by providing an agent for improving the blood circulation, which contains glycosyl vitamin P as an effective ingredient.

The glycosyl vitamin P used in the present invention is a known compound, and similarly as vitamin P it is known that the compound has an activity of inhibiting the permeability of capillaries. The present invention is based on an unexpected finding of the action by glycosyl vitamin P that improves the blood circulation in humans and relieves muscular rigidity independently of the inhibition of capillary permeability. The present invention is novel in that it provides a use of glycosyl vitamin P as an agent for improving the blood circulation.

BRIEF DESCRIPTION OF THE ACCOMPANYING DRAWINGS

DETAILED DESCRIPTION OF THE INVENTION

Figure 1:
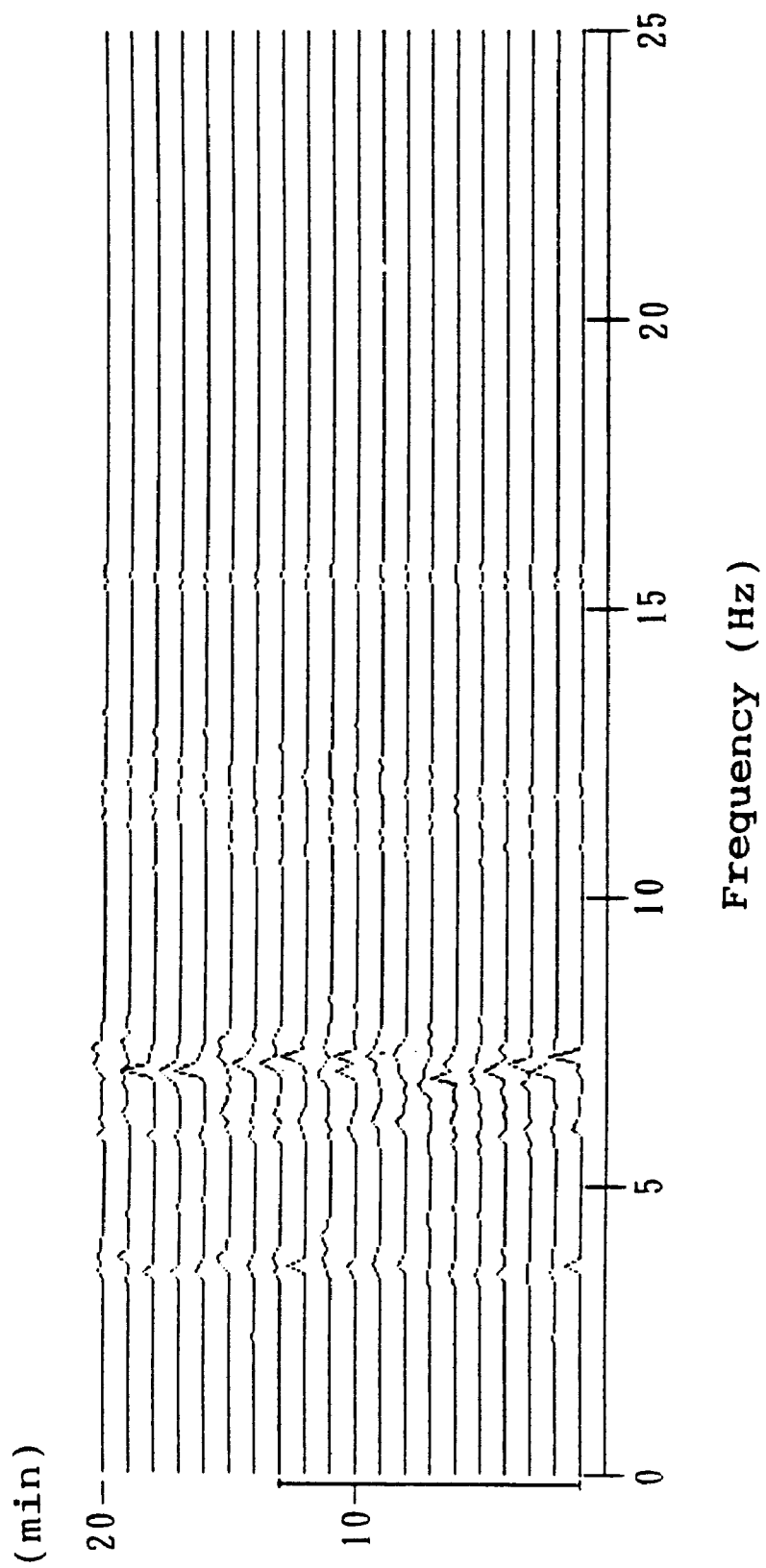
FIG. 1 is a figure that shows an MV pattern detected from a volunteer's dorsum cucullaris just before a cataplasm containing glycosyl vitamin P was attached to the volunteer.

The present invention relates to an agent for improving the blood circulation, which contains glycosyl vitamin P as an effective ingredient. The glycosyl vitamin P used in the present invention usually includes glycosyl hesperidins such as a series of α-monoglucosyl hesperidin, α-diglucosyl hesperidin, α-triglucosyl hesperidin, α-tetraglucosyl hesperidin, and α-pentaglucosyl hesperidin; and glycosyl rutins such as a series of α-monoglucosyl rutin, α-diglucosyl rutin, α-triglucosyl rutin, α-tetraglucosyl rutin, and α-pentaglucosyl rutin. Since these compounds exert substantially the same level of activity of improving the blood circulation, the present agent should contain one or more of them in an effective amount in total. In this connection, glycosyl hesperidin is superior to glycosyl rutin when compared with their activity on relieving muscular rigidity accompanied by lumbagos and muscular pains and on treating diseases with muscular rigidity.

The glycosyl vitamin P can be prepared by different methods. With an economical viewpoint, biochemical methods using saccharide-transferring enzymes are advantageous; The aforesaid series of glycosyl vitamin P can be obtained in a relatively-high yield by contacting vitamin P such as hesperidin and rutin with saccharide-transferring enzymes such as α-glucosidase, cyclomaltodextrin glucanotransferase, and α-amylase in the presence of α-glucosyl saccharides such as partial starch hydrolysates and maltooligosaccharides. The reaction products thus obtained usually contain a series of glycosyl vitamin P compounds with glucose polymerization degrees of 1–5 in terms of transferred glucoses. These compounds can be hydrolyzed into α-monoglucosyl vitamin P by the action of glucoamylase and optionally in combination with rhamnosidase. Methods using saccharide-transferring enzymes are disclosed in detail in Japanese Patent Kokai Nos. 7,593/91, 27,293/91, 58,790/91, and 115,292/91 applied by the same applicant as the present invention; and Japanese Patent Application Nos. 104,272/97, 22,667/97, and 69,588/97 by the same applicant as the present invention. Examples of commercialized products prepared by these methods are "αG RUTIN", a powdery glycosyl rutin product with a total rutin content of 40–82%, on a dry solid basis (d.s.b.), commercialized by Hayashibara Shoji, Inc., Okayama, Japan; and "αG HESPERIDIN", a powdery glycosyl hesperidin product with a total hesperidin content of 22–84%, d.s.b., commercialized by Hayashibara Shoji, Inc., Okayama, Japan. The glycosyl vitamin P used in the present invention should not necessarily be in a highly-purified form or may be in the form of a composition unseparated from other specific substances inherent to the preparation methods used.

As described above, the activity of improving the blood circulation by glycosyl vitamin P is significantly augmented in the presence of trehalose, which trehalose also stabilizes the glycosyl vitamin P, facilitates the administration of the compound, and exerts an activity of promoting the absorption of the compound. Since there found no natural system where glycosyl vitamin P coexists with trehalose, the fact that trehalose promotes the effective activities of glycosyl vitamin P was nothing but a completely-unpredictable finding. The present embodiment, where the artificially-produced glycosyl vitamin P and trehalose are artificially combined, is quite novel in this point.

Explaining the trehalose advantageously used in the present invention, there found, as it is well known, three isomers called $\alpha,\alpha$-, $\alpha,\beta$-, and $\beta,\beta$-isomers having different bonding forms. Since these isomers exert a similar promoting activity on glycosyl vitamin P, they can be used in the present agent for improving the blood circulation independently of their preparation, purity, and property as long as one or more of them are incorporated into the present agent in an effective amount in total.

Trehalose can be produced by a variety methods. Detailed descriptions of such methods are given up because this invention in itself does not relate thereunto. However, considering economical benefit, preferable methods are those which comprise of contacting partial starch hydrolysates with a non-reducing saccharide-forming enzyme and a trehalose-releasing enzyme as disclosed in Japanese Patent Kokai Nos. 143,876/95, 213,283/95, 322,883/95, 298,880/95, 66,187/96, 66,188/96, 336,388/96, and 84,586/96. According to these methods, $\alpha,\alpha$-trehalose can be produced from starches as costless materials in a relatively-high yield; Examples of commercialized products obtained thereby are "TREHAOSE®", a crystalline trehalose powder containing at least 98% trehalose, d.s.b., commercialized by Hayashibara Shoji, Inc., Okayama, Japan; and "TREHASTAR®", a trehalose syrup containing at least 28% trehalose, d.s.b., commercialized by Hayashibara Shoji, Inc., Okayama, Japan. $\alpha,\alpha$-Trehalose can be produced by contacting partial starch hydrolysates either with a maltose/trehalose converting enzyme as disclosed in Japanese Patent Kokai Nos. 149,980/96 and 9,986/97 or with conventionally known maltose-and trehalose-phosphorylases in combination.

To produce $\alpha,\beta$-trehalose, cyclomaltodextrin glucanotransferase and $\beta$-galactosidase are allowed in this order to contact with mixtures of partial starch hydrolysates and lactose according to the methods as disclosed in Japanese Patent Kokai Nos. 144,694/92 and 179,490/92 applied by the same applicant as the present invention. Similarly as glycosyl vitamin P, the trehalose used in the present invention should not necessarily be in a highly-purified form or may be in the form of a composition unseparated from other specific substances inherent to the preparation methods used. Depending on use, the present agent contains trehalose in an amount of at least five-fold higher, and preferably 50-fold or higher than that of glycosyl vitamin P, d.s.b.

The agent according to the present invention includes those which consist of glycosyl vitamin P and those in the form of compositions comprising glycosyl vitamin P and another ingredients which ease the administration of glycosyl vitamin P. The above compositions are usually commercialized in the form of a liquid, paste or solid food product or pharmaceutical. The agent in the form a food product can be prepared into a composition comprising materials and/or ingredients used generally in food products such as water, alcohols, amylaceous substances, fibers, saccharides, lipids, vitamins, minerals, flavors, colors, sweeteners, seasonings, stabilizers, and preservatives. The agent in the form a pharmaceutical can be prepared into a composition comprising carriers, excipients, adjuvants, diluents, and stabilizers, and optionally one or more of other biologically active substances such as tocopherol, acetic retinol, pyridoxine hydrochloride, glycine, ethanol, nicotinamide, licorice extract, and extract of *Angelica acutiloba*. Independently of the aforementioned forms, the present agent usually contains at least 0.001 w/w % glycosyl vitamin P, and preferably 0.01–10 w/w %. As already explained, trehalose effectively facilitates the administration of glycosyl vitamin P.

Explaining the use of the present agent for improving the blood circulation, it exerts a remarkable activity of improving the blood circulation independently of the oral- and parenteral-administrations. Depending on use, in the case of maintaining and promoting health and preventing diseases, the present agent is usually administered orally in the form of a food product, while in the case of treating diseases and recovering health from unsatisfiable health conditions, the present agent is usually administered orally in the form of a pharmaceutical or food product, or administered parenterally in the form of an injection or external medicament. The dose of the present agent is about one milligram to about one gram per shot per adult, and preferably 10 mg to 10 g per shot per adult in terms of glycosyl vitamin P at an administration frequency of 1–4 shots/day or 1–5 shots/week.

Based on the following experiments the effect and toxicity of the present agent are described:

Experiment 1

Relaxation of Muscular Rigidity

A cataplasm containing glycosyl vitamin P was prepared and evaluated on the effect when administered to patient suffering from stiffness in the shoulder based on the basis of micro-vibration (hereinafter abbreviated as "MV") and plethysmogram or volume pulse wave (hereinafter abbreviated as "PTG"). MV is an apparatus for recording microvibration of ballistic components accompanied by muscular fibers in vivo and heartbeat by converting the microvibration into an electrodynamic phenomenon where peaks are detected at a high-frequency region in patients with muscular rigidity such as stiffness in the shoulder, and the peaks are shifted to a lower-frequency region as the muscular rigidity is relived. PTG is an apparatus for detecting blood flow as a vascular change in pressure and for expressing change in volume as a wave-height level; When the wave-height level is increased as the increment of blood flow in a stiff part in the shoulder, meaning that blood circulation is improved. The judgement whether the administration of glycosyl vitamin P improved blood circulation and relieved muscular rigidity can be objectively evaluated by MV and PTG after the administration. The significance and measurement of MV and PTG are described in detail, for example, in *Bulletin of the University of Tsukuba, School for the Blind*, Vol. 16, pp. 75–83 (1983), and "*Rinsho-Kensa-Koza*" (Clinical Testing Course), Vol. 11, pp. 115–135 (1985), published by Ishiyaku Shuppan Publishers, Inc., Tokyo, Japan.

Explaining the particulars of the experiment, a 48-year-old male volunteer suffering from the stiffness in both shoulders was quietly lain face down on a bed after attaching pickups for detecting MV and PTG to a line of dorsum cucullaris with a surgical tape. The patient was monitored for both MV and PTG by a polygraph for 20 min, and the data were recorded by a data recorder. Thereafter, the patient was allowed to sleep well overnight for about eight hours after the pickups were removed from the patient, and either a cataplasm prepared by the method in the later described Example 7 or a placebo as a control prepared similarly as above except for omitting glycosyl vitamin P was attached to the patient.

On the next morning, the cataplasm was removed from the volunteer while he was allowed to lay on the bed, followed by attaching pickups to the same part as of the cataplasm for measuring and recording MV and PTG for 30 min and for two hours, respectively, similarly as above. The measured and recorded MV and PTG were data processed by a signal processor to determine the effectivity of glycosyl vitamin P. The measurement of MV and PTG conducted were as follows: Using "MODEL MT-3T" and "MODEL 45261", which are respectively an MV and PTG pickups commercialized by NEC San-ei Instrument Ltd., Tokyo, Japan, the data obtained from "MODEL 97A", a polygraph commercialized by NEC San-ei Instrument Ltd., Tokyo, Japan, connected with the pickups, was first recorded by "MODEL XR-710", a data recorder commercialized by Teac Corporation, Tokyo, Japan, then appropriately data-processed with "MODEL 7T18A", a signal processor commercialized by NEC San-ei Instrument Ltd., Tokyo, Japan, to determine MV pattern and PTG. The MV patterns before and after the attachment of a cataplasm, prepared by the method in later described Example 7, are respectively in FIGS. 1 and 2. The axis of ordinates in these figures means a relative value of voltage, obtained by appropriately amplifying the in vivo signals detected in the volunteer.

Figure 2:
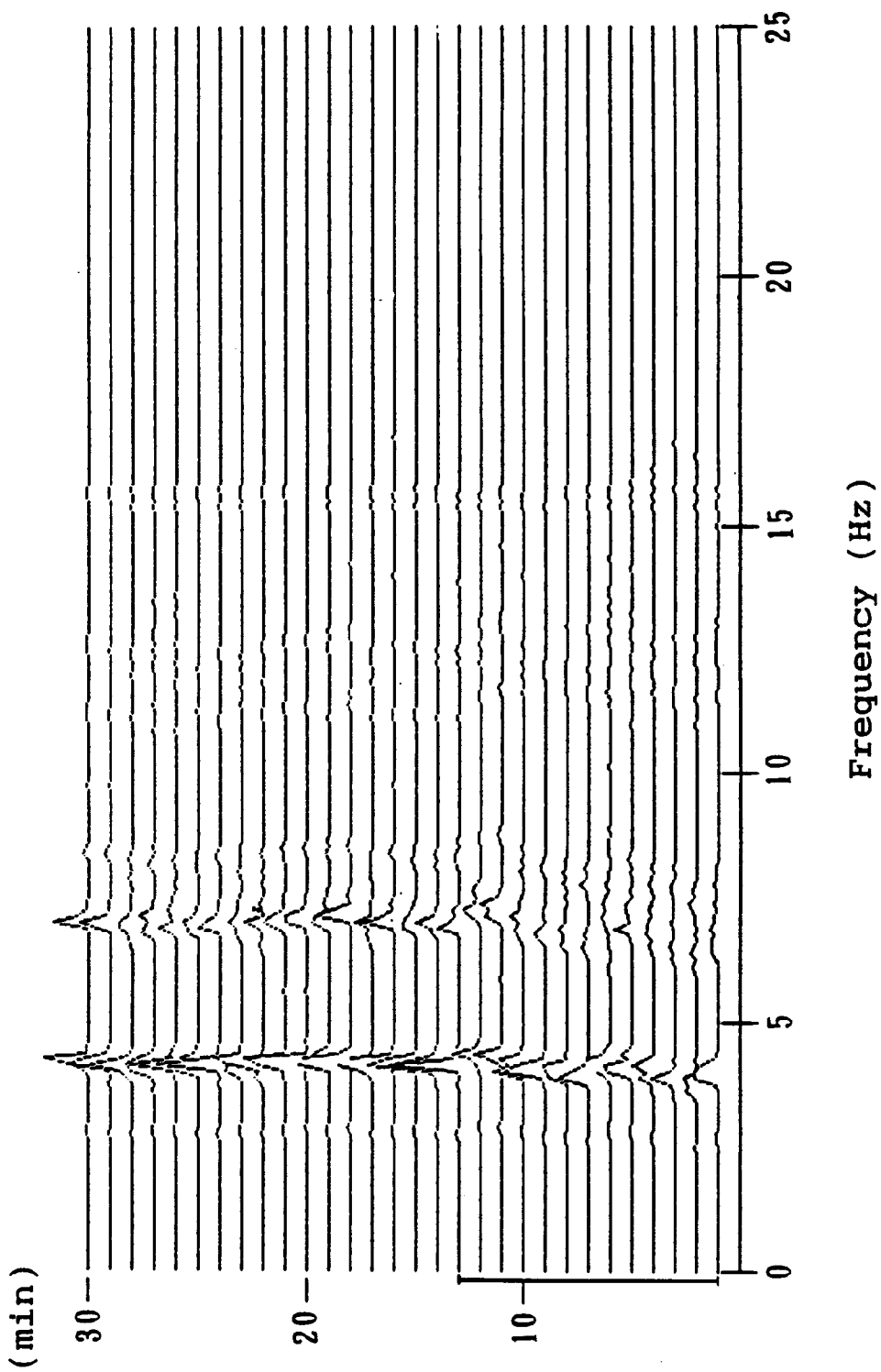
FIG. 2 is a figure that shows an MV pattern detected from a volunteer's dorsum cucullaris just after a cataplasm containing glycosyl vitamin P has been attached to the volunteer for about eight hours.

As shown in FIG. 1, the MV pattern before the attachment of the cataplasm exhibited a relatively-strong peak characteristic of muscular rigidity at a high frequency of around seven hertz, confirming that the volunteer was in a typical state of stiffness in the shoulder. However, as shown in FIG. 2, the MV pattern eight hours after the attachment of the cataplasm containing glycosyl vitamin P exhibited substantially no high-frequency peak but in turn it exhibited a strong peak for a lower frequency of around four hertz characteristic of muscular relief. As not shown in figure, the MV pattern as a control still exhibited the peak characteristic of muscular rigidity even after an eight-hour-sound-sleep similarly as in FIG. 1. The result evidences that glycosyl vitamin P is effective for relieving muscular rigidity caused by stiffness in the shoulder.

Referring to PTG, it turned to be in the range from about 270% to about 300% after the experiment of eight-hour-attachment of the cataplasm containing glycosyl vitamin P. In the control where the placebo was attached, a similar PTG was still observed as just before the experiment even after an eight-hour-sound sleep. The change of PTG was successively observed for about two hours after the cataplasm containing glycosyl vitamin P was detached, revealing that if the blood circulation is once improved, the condition is satisfactorily kept at a relatively-high level through over the observation period. The results confirm that glycosyl vitamin P is effective for improving the blood circulation in humans and that the effect will last for a relatively-long period of time. Similar experiment on vitamin P substantially showed no remarkable effect as compared with control. The reason is that an effective amount of vitamin P was not absorbed by living bodies because of its relatively-low water-solubility.

Experiment 2

Clinical Test

Based on the data of Experiment 1, 60 male volunteers, ranging from 28 to 51 years old, who were suffering from lumbago or chronic stiffness in the shoulder, were subjected to a clinical experiment. Three groups, each of which consisted of 10 randomly-chosen-male-volunteers, were provided and treated with the following treatment for a week; At every night before sleeping, the volunteers were attached with either a cataplasm as an embodiment No. 1 according to the present invention, prepared by the later described method in Example 7; a cataplasm as an embodiment No. 2 according to the present invention, similarly prepared by the method in Example 7 except for replacing trehalose with sucrose; or a placebo as a control similarly prepared by the method in Example 7 except for omitting glycosyl vitamin P, and then replacing the cataplasm with fresh one every following night before sleeping. A clinical paramedic conducted the experiment and, after the experiment, asked the therapeutic effect and the side effects of the volunteers. The therapeutic effect was evaluated with four ranks of "very effective", "effective", "unchanged", and "worsened", and the effectivity (%) was calculated as a percentage of the number of volunteers, who answered "very effective" and "effective", to the total number of volunteers. The results are in Table 1.

TABLE 1

| Answer | Embodiment No. 1 according to the present invention | Embodiment No. 2 according to the present invention | Control |
| --- | --- | --- | --- |
| Very effective | 2 | 1 | 0 |
| Effective | 4 | 4 | 2 |
| Unchanged | 3 | 4 | 7 |
| Worsened | 1 | 1 | 1 |
| Effectivity (%) | 60 | 50 | 20 |

Note:
Embodiment Nos. 1 and 2 mean an agent for improving the blood circulation containing glycosyl vitamin P and trehalose according to the present invention, and an agent for improving the blood circulation containing glycosyl vitamin P according to the present invention, resspectively.

In parallel three groups, each of which consisted of 10 volunteers who were randomly chosen from the resting 30 volunteers, were provided and orally administered every day and every meal for a week with three same tablets of either a tablet as an embodiment No. 3 according to the present invention, prepared by the later described method in Example 5; a tablet as an embodiment No. 4 similarly prepared by the method in Example 5 except for replacing trehalose with sucrose; or a tablet as a placebo similarly prepared by the method in Example 5 except for omitting glycosyl vitamin P. A clinical paramedic conducted the experiment and, at 24 hours after the final administration, asked the therapeutic effect and the side effects of the volunteers. The therapeutic effect was similarly evaluated as in the above criteria of four ranks. The results are in Table 2.

TABLE 2

| Answer | Embodiment No. 3 according to the present invention | Embodiment No. 4 according to the present invention | Control |
| --- | --- | --- | --- |
| Very effective | 1 | 1 | 0 |
| Effective | 4 | 3 | 1 |
| Unchanged | 5 | 5 | 9 |

TABLE 2-continued

| Answer | Embodiment No. 3 according to the present invention | Embodiment No. 4 according to the present invention | Control |
|---|---|---|---|
| Worsened | 0 | 1 | 0 |
| Effectivity (%) | 50 | 40 | 10 |

Note:
Embodiment Nos. 3 and 4 mean an agent for improving the blood circulation containing glycosyl vitamin P and trehalose according to the present invention, and an agent for improving the blood circulation containing glycosyl vitamin P according to the present invention, respectively.

The results in Tables 1 and 2 evidence that glycosyl vitamin P has an activity of effectively relieving muscular rigidity induced by lumbago and stiffness in the shoulder when administered to humans independently of its administration route with lesser side effects, and that the activity is significantly augmented by trehalose, a specific saccharide among various saccharides. Preliminary experiments on symptoms other than lumbago and stiffness in the shoulder revealed that glycosyl vitamin P exerts a strong effect on muscular pains, neuralgias, sprains, feelings of cold, frostbites, bruises, arthritis, neuritis, tendovaginitis, asthenopia, arteriosclerosis, etc.

Experiment 3
Acute Toxicity Test

An adequate amount of "TREHAOSE®", a crystalline trehalose powder commercialized by Hayashibara Shoji, Inc., Okayama, Japan, was dissolved in physiological saline containing 5 w/w % gum arabic, and the solution was sterilized in usual manner and intraperitoneally injected to ddy-mice, 20–25 g weight, in a group of 10 mice, or orally administered to the mice by using a stomach sonde. Thereafter, the mice were observed for a week. As a result, no mouse died even administered with a dose of about 16 g per kg mouse as a maximum dose challenged, independently of its administration route. In parallel similar experiments were conducted using as glycosyl vitamin P "αG HESPERIDIN PA" with a total hesperidin content of 74–78%, d.s.b., a glycosyl hesperidin power commercialized by Hayashibara Shoji, Inc., Okayama, Japan, and "αG RUTIN PS" with a total rutin content of 80–82%, d.s.b., a glycosyl rutin powder commercialized by Hayashibara Shoji, Inc., Okayama, Japan. As a result, no mouse died up to a dose of about five grams per kg mouse as a maximum dose challenged.

The results in Experiments 1–3 evidence that the present agent for improving the blood circulation is effectively administered to humans with lesser side effects.

With reference to the following Examples, the preferred embodiments according to the present invention are described as follows:

EXAMPLE 1
Health Food

One hundred and fifty parts by weight of "TREHASTAR®", a trehalose syrup commercialized by Hayashibara Shoji, Inc., Okayama, Japan, was heated and concentrated in vacuo up to give a moisture content of about 15 w/w %. The concentrate was mixed with a solution obtained by dissolving 13 parts by weight of gelatin in 18 parts by weight of water, one part by weight of "αG HESPERIDIN H" with a total hesperidin content of 22–26%, a glycosyl hesperidin powder commercialized by Hayashibara Shoji, Inc., Okayama, Japan, two parts by weight of citric acid, and adequate amounts of a coloring agent and a flavor, and the resulting mixture was shaped and packed to obtain a gummy candy.

The product with a satisfactory texture and flavor is useful as a health food that improves/maintains the blood circulation to relieve and/or prevent muscular rigidity caused by lumbago, stiffness in the shoulder, muscular pains, etc.

EXAMPLE 2
Health Food

Three parts by weight of a gum base was melted by heating until softened, mixed with seven parts by weight of "NUMIX", a powdered green and yellow vegetable with a trehalose content of about 50 w/w %, commercialized by H+B Life Science Co., Ltd., Okayama, Japan; adequate amounts of a coloring agent and a flavor; and "αG RUTIN P", a glycosyl rutin powder with a total rutin content of 40–46%, d.s.b., in an amount sufficient to be brought up to a content of 0.1%, d.s.b., and the resulting mixture was in usual manner kneaded, shaped, and packed to obtain a chewing gum containing glycosyl vitamin P.

The product with a satisfactory texture and taste is useful as a health food that improves/maintains the blood circulation to relieve and/or prevent muscular rigidity caused by lumbago, stiffness in the shoulder, muscular pains, etc.

EXAMPLE 3
Health Food

Eighty-six parts by weight of skim milk, three parts by weight of skim milk powder, nine parts by weight of "TREHASTAR®", a trehalose syrup commercialized by Hayashibara Shoji, Inc., Okayama, Japan, 0.1 part by weight of agar, 0.1 part by weight of "αG HESPERIDIN PA", a glycosyl hesperidin powder with a total hesperidin content of 74–78%, d.s.b., commercialized by Hayashibara Shoji, Inc., Okayama, Japan, and 1.8 parts by weight of water were placed in a tank and heated to 55° C. to completely dissolve the contents under stirring conditions. Thereafter, the mixture was homogenized in usual manner, sterilized by a sterilizing cooler, inoculated with three w/w % of a starter, injected into a plastic container, and fermented at 37° C. for five hours into a yogurt containing glycosyl vitamin P.

The product with a satisfactory flavor and taste is useful as a health food that improves/maintains the blood circulation to relieve or prevent muscular rigidity caused by lumbago, stiffness in the shoulder, muscular pains, etc.

EXAMPLE 4
Supplemental Health Food

One part by weight of "αG HESPERIDIN PA", a glycosyl hesperidin powder with a total hesperidin content of 74–78%, d.s.b., commercialized by Hayashibara Shoji, Inc., Okayama, Japan, and 99 parts by weight of "TREHAOSE®", a crystalline trehalose powder commercialized by Hayashibara Shoji, Inc., Okayama, Japan, were mixed to homogeneity, and 50 g aliquots of the resulting mixture were injected into glass vials to obtain the desired product.

About one gram of the product is spooned up for eating directly or for drinking after dissolved in water for ease of a supplement of about 10 mg glycosyl vitamin P to the body. The product with a superior solubility and handle ability is useful as a supplementary health food that improves/maintains the blood circulation to relive and/or prevent muscular rigidity caused by lumbago, stiffness in the shoulder, muscular pains, etc.

EXAMPLE 5

Tablet

Ten parts by weight of "AA-2G", a glycosyl vitamin C powder commercialized by Hayashibara Shoji, Inc., Okayama, Japan, three parts by weight of "αG HESPERIDIN PA", a glycosyl hesperidin powder with a total hesperidin content of 74–78%, d.s.b., commercialized by Hayashibara Shoji, Inc., Okayama, Japan, and 17 parts by weight of "TREHAOSE®", a crystalline trehalose powder commercialized by Hayashibara Shoji, Inc., Okayama, Japan, were mixed to homogeneity. The mixture was tabletted in usual manner to obtain a tablet containing 10 mg glycosyl vitamin P.

The product, having a readily swallowability and solubility and a vitamin C-supplementing action, is useful as a tablet that improves/maintains the blood circulation to relive and/or prevent muscular rigidity caused by lumbago, stiffness in the shoulder, muscular pains, etc.

EXAMPLE 6

Solution

In 1,000 parts by weight of distilled water were dissolved six parts by weight of sodium chloride, 0.3 part by weight of potassium chloride, 0.2 part by weight of calcium chloride, 3.1 parts by weight of sodium lactate, 44 parts by weight of "TREHAOSE®", a crystalline trehalose powder commercialized by Hayashibara Shoji, Inc., Okayama, Japan, 1.5 parts by weight of "αG HESPERIDIN PS", a glycosyl hesperidin powder with a total hesperidin content of 80–84%, d.s.b., commercialized by Hayashibara Shoji, Inc., Okayama, Japan, and 0.5 part by weight of "AA-2G®", a glycosyl vitamin C commercialized by Hayashibara Shoji, Inc., Okayama, Japan. The resulting solution was filtered in usual manner, and 25 ml aliquots of the filtrate were injected into plastic containers to obtain a solution containing glycosyl vitamin P.

The product, having an activity of supplementing vitamins, calories, and minerals, is used as a collyrium or injection for treating symptoms with asthenopia and/or heavy muscular rigidity.

EXAMPLE 7

Cataplasm

One part by weight of crotamiton and 0.3 part by weight of "αG HESPERIDIN PS", a glycosyl hesperidin powder with a total hesperidin content of 80–84%, d.s.b., commercialized by Hayashibara Shoji, Inc., Okayama, Japan, were heated in water bath. While dissolving by mixing into a solution, 45.2 parts by weight of distilled water, 10 parts by weight of "TREHAOSE®", a crystalline trehalose powder commercialized by Hayashibara Shoji, Inc., Okayama, Japan, five parts by weight of gelatin, and seven parts by weight of kaolin were placed in a mixer and heated to about 50° C. into a homogeneously dispersed solution. To the solution was added another dispersed solution of 25 parts by weight of glycerine, three parts by weight of sodium polyacrylate, and 3.5 parts by weight of carboxy methyl cellulose. The solution thus obtained was mixed while stirring to obtain a homogeneously-kneaded mixture.

The resulting product was added to the above dissolved solution and kneaded to homogeneity under stirring conditions. The newly obtained mixture was applied over a nonwoven fabric to form a film with one millimeter thick by using a spreader. After overlaying with a polypropylene sheet one side of the above fabric applied with the solution, the resulting fabric was cut in a prescribed size into the desired product.

The product gives substantially no unsatisfiable feeling when attached to the skin, and the effect lasts for a relatively-long period of time. Thus the product is useful as a cataplasm that relives muscular rigidity caused by lumbago, stiffness in the shoulder, muscular pains, etc., and that treats symptoms with muscular rigidity.

As described above, the present invention was made based on the self-finding that glycosyl vitamin P improves the blood circulation in humans to effectively relieve muscular rigidity. The present agent for improving the blood circulation exerts a remarkable effect on the recovery of mental and physical spirits from fatigue and treats/prevents diseases and symptoms such as stiffness in the shoulder, lumbagos, muscular pains, neuralgias, bruises, sprains, arthritis, neuritis, tendovaginitis, cervical spondylosis, thoracic outlet syndrome, asthenopia, feelings of cold, frostbites, arteriosclerosis, autonomic dystonia, and climacteric disturbance.

The present agent effectively acts on diseases induced by the disorder or the cease of blood circulation such as congestion, diminishes or extinctions the disorder or the cease of blood circulation where the advancement of diseases do not accompany blood coagulation or tissue necrosis, and effectively prevents circulatory diseases such as hypertension, arteriosclerosis, cerebral hemorrhage, cerebral thrombosis, cerebral embolism, subarachnoid hemorrhage, cerebral ischemia paroxysm, hypertensive encephalopathy, cerebral infarction, myocardial ischemia, myocardial infarction, and angina pectoris.

While there has been described what is at present considered to be the preferred embodiments of the invention, it will be understood the various modifications may be made therein, and it is intended to cover in the appended claims all such modifications as fall within the true spirits and scope of the invention.

We claim:

1. A composition for improving blood circulation, comprising an amount sufficient of glycosyl vitamin P and trehalose in a unit dosage form for improving blood circulation, together with a carrier for said glycosyl vitamin P and said trehalose, and wherein said carrier is optionally edible.

2. The composition of claim 1, wherein said glycosyl vitamin P is in the form of glycosyl hesperidin, glycosyl rutin, or a mixture thereof.

3. The composition of claim 1, wherein said glycosyl vitamin P is present in an amount of at least 0.001 w/w %.

4. A composition according to claim 1, wherein said trehalose is α,α-, α,β- or β,β-trehalose.

5. A composition according to claim 4, wherein said edible carrier is a food material or a food ingredient.

6. A composition according to claim 5, wherein said trehalose is present in an amount at least 5-fold higher than that of said glycosyl vitamin P, on a dry solid basis.

7. A composition according to claim 1, wherein said trehalose is present in an amount at least 5-fold higher than that of said glycosyl vitamin P, on a dry solid basis.

8. A composition according to claim 1, wherein said edible carrier is a food material or a food ingredient.

9. A composition according to claim 1, in the form of a pharmaceutical composition in unit dosage form suitable for oral or parenteral administration, wherein said carrier is pharmaceutically acceptable carrier or excipient.

10. The composition of claim 9, wherein said glycosyl vitamin P is in the form of glycosyl hesperidin, glycosyl rutin, or a mixture thereof.

11. The composition of claim 9, wherein said glycosyl vitamin P is present in an amount of at least 0.001 w/w %.

12. A composition according to claim 9, wherein said trehalose is α,α, α,β- or β,β-trehalose.

13. The composition according to claim 9, wherein said trehalose is present in an amount at least 5-fold higher than that of said glycosyl vitamin P, on a dry solid basis.

14. A method for relieving muscular rigidity in a patient in need of said therapy, comprising administering to said patient an amount effective for said therapy or a muscular-rigidity lenitive comprising glycosyl vitamin P.

15. A method according to claim 14, wherein said glycosyl vitamin P comprises glycosyl hesperidin, glycosyl rutin, or a mixture thereof.

16. A method according to claim 14 comprising administering said glycosyl vitamin P in a unit dosage form in a pharmaceutical composition containing at least 0.001 w/w % of said glycosyl vitamin P together with a pharmaceutically acceptable carrier.

17. A method according to claim 16, wherein said administration is orally or parenterally.

18. A method according to claim 16, wherein said glycosyl vitamin P is administered together with trehalose.

19. A method according to claim 18, wherein said trehalose is administered in an amount of at least 5-fold higher than that of said glycosyl vitamin P, on a dry solid basis.

20. A method according to claim 18, wherein said trehalose is $\alpha,\alpha$-, $\alpha,\beta$- or $\beta,\beta$-trehalose.

* * * * *